(12) United States Patent
Zheng et al.

(10) Patent No.: US 11,345,879 B2
(45) Date of Patent: *May 31, 2022

(54) EMULSION STEREOLITHOGRAPHY AND 3D PRINTING OF MULTIMATERIALS AND NANOSCALE MATERIAL GRADIENTS

(71) Applicant: LAWRENCE LIVERMORE NATIONAL SECURITY, LLC, Livermore, CA (US)

(72) Inventors: Xiaoyu Zheng, Pleasanton, CA (US); Joshua R. Deotte, Livermore, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 489 days.

This patent is subject to a terminal disclaimer.

(21) Appl. No.: 14/943,873

(22) Filed: Nov. 17, 2015

(65) Prior Publication Data

US 2017/0136692 A1 May 18, 2017

(51) Int. Cl.

| | |
|---|---|
| *B33Y 10/00* | (2015.01) |
| *C12M 3/00* | (2006.01) |
| *C12N 5/00* | (2006.01) |
| *C12M 1/42* | (2006.01) |
| *B29C 64/135* | (2017.01) |
| *C12M 1/12* | (2006.01) |
| *C12N 5/071* | (2010.01) |
| *B29C 64/20* | (2017.01) |
| *B33Y 30/00* | (2015.01) |
| *B33Y 50/02* | (2015.01) |
| *B29C 35/08* | (2006.01) |
| *B29K 105/00* | (2006.01) |
| *B29L 31/34* | (2006.01) |
| *B29L 31/00* | (2006.01) |
| *B29C 64/386* | (2017.01) |

(52) U.S. Cl.
CPC .......... *C12M 21/08* (2013.01); *B29C 64/135* (2017.08); *B29C 64/20* (2017.08); *B33Y 10/00* (2014.12); *C12M 25/14* (2013.01); *C12M 35/08* (2013.01); *C12N 5/0062* (2013.01); *C12N 5/0697* (2013.01); *B29C 64/386* (2017.08); *B29C 2035/0827* (2013.01); *B29K 2105/0061* (2013.01); *B29L 2031/34* (2013.01); *B29L 2031/7532* (2013.01); *B33Y 30/00* (2014.12); *B33Y 50/02* (2014.12)

(58) Field of Classification Search
CPC .............. B29C 67/0059; B29C 64/20; B29C 2035/0827; B33Y 10/00; B33Y 30/00; B33Y 50/02; C12M 21/08; C12M 25/14; C12N 5/0697; C12N 5/0062; B29K 2105/0061

See application file for complete search history.

(56) References Cited

U.S. PATENT DOCUMENTS

| | | |
|---|---|---|
| 4,575,330 A | 3/1986 | Hull |
| 8,197,743 B2 | 6/2012 | Wicker et al. |
| 10,286,600 B2 * | 5/2019 | Deotte ................. B29C 64/124 |
| 2014/0257518 A1 * | 9/2014 | McAlpine ................ A61F 2/18 623/24 |
| 2015/0307728 A1 * | 10/2015 | Omenetto .............. C09D 11/04 424/649 |

OTHER PUBLICATIONS

Landers "Desktop manufacturing of complex objects, prototypes and biomedical scaffolds by means of computer-assisted design combined with computer-guided 3D plotting of polymers and reactive oligomers" Macromol. Mater. Eng. 2000, 282, 17-21.*
Arcaute et al. Annals of Biomedical Engineering, vol. 34, No. 9, Sep. 2006 pp. 1429-1441.*
Arcaute et al. Annals of Biomedical Engineering, vol. 34, No. 9, Sep. 2006 pp. 1429-1441 (Year: 2006).*
Desktop manufacturing of complex objects, prototypes and biomedical scaffolds by means of computer-assisted design combined with computer-guided 3D plotting of polymers and reactive oligomers Macromol. Mater. Eng. 2000, 282, 17-21 (Year: 2000).*
Zheng et al. Rev. of Scientific Instr., 83, 2012, pp. 125001-1 to 125001-6 (Year: 2012).*
Zheng et al., "Design and Optimizing of a Light-Emitting Diode Projection Micro-Stereolithography Three-Dimensional Manufacturing System," Rev. of Scientific Instr., 83, 2012, pp. 125001-1 to 125001-6.

* cited by examiner

*Primary Examiner* — Olivia M. Wise
*Assistant Examiner* — Anjali Ajit Hirani
(74) *Attorney, Agent, or Firm* — Eddie E. Scott

(57) ABSTRACT

A functionally graded material is formed by pipetting individual micro-or-nano-litter droplets with a variety of materials including multi-nanostructured material (nanowires, carbon nanotubes, enzymes, multi-element and/or multi-color, multi-biomolecules) and UV polymerization of the flat hydrogel meniscus surface formed at the carrier fluid interface. After step-by-step droplet pipetting and subsequent layer-by-layer UV polymerization via a digital mask, the complete fabricated part without supporting layers is taken out of the carrier fluid while the un-cured micro-litter residue is conveniently suctioned out of the carrier fluid.

2 Claims, 9 Drawing Sheets

EMULSION STEREOLITHOGRAPHY AND 3D PRINTING OF MULTIMATERIALS AND NANOSCALE MATERIAL GRADIENTS

STATEMENT AS TO RIGHTS TO APPLICATIONS MADE UNDER FEDERALLY SPONSORED RESEARCH AND DEVELOPMENT

The United States Government has rights in this application pursuant to Contract No. DE-AC52-07NA27344 between the United States Department of Energy and Lawrence Livermore National Security, LLC for the operation of Lawrence Livermore National Laboratory.

BACKGROUND

Field of Endeavor

The present application relates to additive manufacturing and more particularly to printing of multimaterials and nanoscale material gradients.

State of Technology

This section provides background information related to the present disclosure which is not necessarily prior art.

The journal article, "Design and optimization of a light-emitting diode projection microstereolithography three-dimensional manufacturing system," by Xiaoyu Zheng et al., in *Review of Scientific Instruments*, 83, 125001 (2012) includes the state of technology information reproduced below.

The ability to produce complex, micro-scale, three-dimensional (3D) structures are a major challenge for the manufacturing industry. These types of structures can provide highly functional components for a variety of applications such as bioimplantable devices, sensors and actuators, micro-robots, thermal electronics, and energy efficient structures.

There is a large array of additive methods to fabricate 3D structures. Current manufacturing of 3D microstructures involves highly complex processes such as x-ray lithography, deep UV, LIGA, and soft lithography. In all these manufacturing technologies, the fabrication of the final structures cannot be completed with a single process, and also requires large quantities of sacrificial material. These technologies, developed to fabricate microstructures with high aspect ratios, have not found extensive industrial application due to their limited flexibility and high operational cost.

The journal article, "Design and optimization of a light-emitting diode projection microstereolithography three-dimensional manufacturing system," by Xiaoyu Zheng et al., in *Review of Scientific Instruments*, 83, 125001 (2012) is incorporated herein in its entirety for all purposes by this reference.

U.S. Pat. No. 8,197,743 for hydrogel constructs using stereolithography provides the state of technology information reproduced below.

Rapid prototyping (RP) technologies, also known as Solid Freeform Fabrication (SFF), layered manufacturing and other similar technologies enable the manufacture of complex three-dimensional (3D) parts. RP technologies, in particular, generally construct parts by building one layer at a time. RP technologies are commonly used to build parts and prototypes for use in, for example, the toy, automotive, aircraft and medical industries. Oftentimes prototypes made by RP technologies aid in research and development and provide a low cost alternative to traditional prototyping. In a few cases, RP technologies have been used in medical applications such as those associated with reconstructive surgery and tissue engineering (TE).

Stereolithography (SL) is one of the most widely used RP technologies known in the art. The resolution of SL machines and the ability of SL to manufacture highly complex 3D objects, make SL ideal for building both functional and non-functional prototypes. In particular, SL techniques provide an economical, physical model of objects quickly and prior to making more expensive finished parts. The models are readily customizable and changes may be easily implemented.

SL generally involves a multi-stage process. For example, the first stage involves designing and inputting a precise mathematical geometric description of the desired structure's shape into one of many computer-aided design (CAD) programs and saving the description in the standard transform language (STL) file format. In the second stage, the STL file is imported into SL machine-specific software (RP software). The RP software slices the design into layers and determines the placement of support structures to hold each cross-section in place while building the structure layer by layer. By computing build parameters, the RP software controls the part's fabrication. In the layer preparation stage, the build parameters for the desired part are translated into machine language. Finally, the machine language controls the SL machine to build a desired part and its support structure layer by layer. SL machines typically focus an ultraviolet (UV) laser onto a cross-section of a liquid photopolymer resin. The laser, in turn, selectively cures a resin to form a structure, such as anatomical shapes (i.e., organs and tissues), layer by layer. Ultimately, the part is cleaned, the support structure is removed and the part is post-cured (typically exposed to UV) prior to completion. The operator may, however, need to sand, file or use some other finishing technique on the part in order to provide a specific surface finish to the structure, which may include painting, plating and/or coating the structure's surface.

U.S. Pat. No. 4,575,330 for apparatus for production of three-dimensional objects by stereolithography provides the state of technology information reproduced below.

It is common practice in the production of plastic parts and the like to first design such a part and then painstakingly produces a prototype of the part, all involving considerable time, effort and expense. The design is then reviewed and, oftentimes, the laborious process is again and again repeated until the design has been optimized. After design optimization, the next step is production. Most production plastic parts are injection molded. Since the design time and tooling costs are very high, plastic parts are usually only practical in high volume production. While other processes are available for the production of plastic parts, including direct machine work, vacuum-forming and direct forming, such methods are typically only cost effective for short run production, and the parts produced are usually inferior in quality to molded parts.

In recent years, very sophisticated techniques have been developed for generating three-dimensional objects within a fluid medium which is selectively cured by beams of radiation brought to selective focus at prescribed intersection points within the three-dimensional volume of the fluid medium. Typical of such three-dimensional systems are those described in U.S. Pat. Nos. 4,041,476, 4,078,229, 4,238,840 and 4,288,861. All of these systems rely upon the buildup of synergistic energization at selected points deep within the fluid volume, to the exclusion of all other points in the fluid volume, using a variety of elaborate multibeam techniques. In this regard, the various approaches described in the prior art include the use of a pair of electromagnetic radiation beams directed to intersect at specified coordinates, wherein the various beams may be of the same or differing wavelengths, or where beams are used sequentially to intersect the same points rather than simultaneously, but in all cases only the beam intersection points are stimulated to sufficient energy levels to accomplish the necessary curing process for forming a three-dimensional object within the volume of the fluid medium. Unfortunately, however, such three-dimensional forming systems face a number of problems with regard to resolution and exposure control. The loss of radiation intensity and image forming resolution of the focused spots as the intersections move deeper into the fluid medium create rather obvious complex control situations. Absorption, diffusion, dispersion and defraction all contribute to the difficulties of working deep within the fluid medium on any economical and reliable basis.

Yet there continues to be a long existing need in the design and production arts for the capability of rapidly and reliably moving from the design stage to the prototype stage and to ultimate production, particularly moving directly from computer designs for such plastic parts to virtually immediate prototypes and the facility for large scale production on an economical and automatic basis.

Accordingly, those concerned with the development and production of three-dimensional plastic objects and the like have long recognized the desirability for further improvement in more rapid, reliable, economical and automatic means which would facilitate quickly moving from a design stage to the prototype stage and to production, while avoiding the complicated focusing, alignment and exposure problems of the prior art three dimensional production systems. The present invention clearly fulfills all of these needs.

SUMMARY

Features and advantages of the disclosed apparatus, systems, and methods will become apparent from the following description. Applicant is providing this description, which includes drawings and examples of specific embodiments, to give a broad representation of the apparatus, systems, and methods. Various changes and modifications within the spirit and scope of the application will become apparent to those skilled in the art from this description and by practice of the apparatus, systems, and methods. The scope of the apparatus, systems, and methods is not intended to be limited to the particular forms disclosed and the application covers all modifications, equivalents, and alternatives falling within the spirit and scope of the apparatus, systems, and methods as defined by the claims.

The inventor's apparatus, system and methods provide emulsion stereolithography and 3D printing of multimaterials and nanoscale material gradients. The inventor's apparatus, system and methods provide a three-dimensional fabrication technology based on photo-polymerization reaction of hydrogel droplets in carrier fluids. This enables three-dimensional, multi-material, multi-element and/or multi-color, biocompatible manufacturing of water soluble materials. The base hydrogel material with a variety of functional constituents including different colored dyes, enzymes, nanowires, and biomolecules can be constructed into a material with arbitrary three-dimensional micro-architectures using this technique.

This inventors' apparatus, systems, and methods can be used to fabricate three-dimensional multi-materials with graded functionalities from water-soluble hydrogels. The functionally graded material can be formed by pipetting individual micro- or nano-liter droplet with a variety of materials including multi-nanostructured material (nanowires, carbon nanotubes, enzymes, multi-element and/or multi-color, multi-biomolecules) and UV polymerization of the flat hydrogel meniscus surface formed at the carrier fluid interface. After step-by-step droplet delivery and the subsequent layer-by-layer UV polymerization via a digital mask, the complete fabricated part without supporting layers can be taken out of the carrier fluid while the un-cured microlitter residue can be conveniently suctioned out of the carrier fluid from the water-polymer emulsion system.

The inventor's apparatus, system and methods have many uses. One example is fabricating materials with embedded biomolecules for sensing, actuation, and building of artificial organs. Other examples of uses of the inventor's apparatus, system and methods are described below. It is to be understood that there are many uses in addition to those listed and the inventor's apparatus, system and methods can be used for a wide variety of emulsion stereolithography and 3D printing of products using droplets containing a wide range of materials.

Active 3D electronics to date, 3D printing has been limited to specific plastics, passive conductors, and a few biological materials. The inventors' apparatus, systems, and methods will enable 3D printing of a diverse array of materials within a device component such as quantum dots light emitting device, 3D holographic display and conducting polymers.

Micro-architected materials composed of materials with distinct thermal expansion coefficient can result in zero to negative thermal expansion coefficient. The 3D multi-material component can be used in precision optics in high temperature environment.

Active 3D electronics to date, 3D printing has been limited to specific plastics, passive conductors, and a few biological materials. The inventors' apparatus, systems, and methods will enable 3D printing of a diverse array of materials within a device component such as quantum dots light emitting device, 3D holographic display and conducting polymers.

The inventors' apparatus, systems, and methods enable fabrication of biodegradable stents. Due to the expense of bioresorbable polymers and the difficulty in synthesizing new ones, excess waste volumes should be minimized.

The inventors' apparatus, systems, and methods described uses a tiny (<100 uL) volume of hydrogel for fabrication of initial layers, with additional hydrogel required as the structure is built vertically. Most critically, the volume of the hydrogel is kept close to the volume of the structure.

The inventors' apparatus, systems, and methods enable in-place fabrication of decorated hydrogels for embedded in-situ biochemical sensing. Reagents for immunosorbent assays are typically measured in the microliter range and so traditional 3D printing cannot be used due to excessive material waste or contamination. Since the inventors' apparatus, systems, and methods only require a few microliters for fabrication, small volume of high value reagents can be mixed into hydrogel prepolymer and fabricated in-place within the structure. The inventors' apparatus, systems, and methods enable fabrication of 3D tissue growth scaffold embedded with chemical gradients. The microdosing syringe allows for different hydrogel materials with different chemical gradients to be swapped during fabrication. As the hydrogel is constructed, directed cell growth enabled by 3D patterned chemical gradients can be achieved.

The apparatus, systems, and methods are susceptible to modifications and alternative forms. Specific embodiments are shown by way of example. It is to be understood that the apparatus, systems, and methods are not limited to the particular forms disclosed. The apparatus, systems, and methods cover all modifications, equivalents, and alternatives falling within the spirit and scope of the application as defined by the claims.

BRIEF DESCRIPTION OF THE DRAWINGS

The accompanying drawings, which are incorporated into and constitute a part of the specification, illustrate specific embodiments of the apparatus, systems, and methods and, together with the general description given above, and the detailed description of the specific embodiments, serve to explain the principles of the apparatus, systems, and methods.

DETAILED DESCRIPTION OF SPECIFIC EMBODIMENTS

Referring to the drawings, to the following detailed description, and to incorporated materials, detailed information about the apparatus, systems, and methods is provided including the description of specific embodiments. The detailed description serves to explain the principles of the apparatus, systems, and methods. The apparatus, systems, and methods are susceptible to modifications and alternative forms. The application is not limited to the particular forms disclosed. The application covers all modifications, equivalents, and alternatives falling within the spirit and scope of the apparatus, systems, and methods as defined by the claims.

The inventors' apparatus, systems, and methods solve the problem of relying on a large bath of UV polymer resin as the building base material, and its inability to fabricate multi-materials. The functionally graded material can be formed by pipetting individual micro- or nano-liter droplet with a variety of materials including multi-nanostructured material (nanowires, carbon nanotubes, enzymes, multi-element and/or multi-color, multi-biomolecules) and UV polymerization of the flat hydrogel meniscus surface formed at the carrier fluid interface. After step-by-step droplet pipetting and the subsequent layer-by-layer UV polymerization via a digital mask, the complete fabricated part without supporting layers can be taken out of the carrier fluid while the un-cured micro-litter residue can be conveniently suctioned out of the carrier fluid from the water-polymer emulsion system.

The inventors' apparatus, systems, and methods enable deposition of droplet into the carrier fluid and forming a flat disk on top of the substrate with controlled thickness. The flat UV curable hydrogel disk is then exposed to focus UV light modulated by a digital light modulator and solidified into one solid material with defined geometry. As the carrier fluid filled in the container contains no feedstock building material, an unlimited number of different types of material droplets can be deposited onto the substrate and patterned by a layer-by-layer fashion.

The inventor's apparatus, system and methods provide emulsion stereolithography and 3D printing of multimaterials and nanoscale material gradients. A functionally graded material is formed by pipetting individual micro- or nano-liter droplet with a variety of materials including multi-nanostructured material (nanowires, carbon nanotubes, enzymes, multi-element and/or multi-color, multi-biomolecules) and UV polymerization of the flat hydrogel meniscus surface formed at the carrier fluid interface. After step-by-step droplet pipetting and subsequent layer-by-layer UV polymerization via a digital mask, the complete fabricated part without supporting layers is taken out of the carrier fluid while the un-cured micro-litter residue is conveniently suctioned out of the carrier fluid.

Referring to the drawings and in particular to FIGS. 1A through 1H, one embodiment of the disclosed stereolithography and 3D printing of multimaterials and nanoscale material gradients system is illustrated. This embodiment is designated generally by the reference numeral 10.

FIGS. 1A through 1H provide schematic depictions illustrating the system 10. FIGS. 1A through 1H show the structural elements identified and described below.

Reference numeral 10—stereolithography and 3D printing of multimaterials and nanoscale material gradients system
Reference numeral 12—reservoir
Reference numeral 14—carrier fluid
Reference numeral 16—elevator system
Reference numeral 18—substrate
Reference numeral 20—first droplet
Reference numeral 22—droplet dispenser
Reference numeral 24—first layer image
Reference numeral 28—first layer
Reference numeral 30—second droplet
Reference numeral 32—second layer image
Reference numeral 34—second layer
Reference numeral 36—third droplet
Reference numeral 38—third layer image
Reference numeral 40—third layer The structural elements of the system 10 having been identified and described, the operation of the system 10 will now be considered. A 3D model of the end product is created and the model is sliced into individual layers. The first layer is sent to a projection system and subsequently projected to the appropriate locations as image to build the product.

Figure 1A:
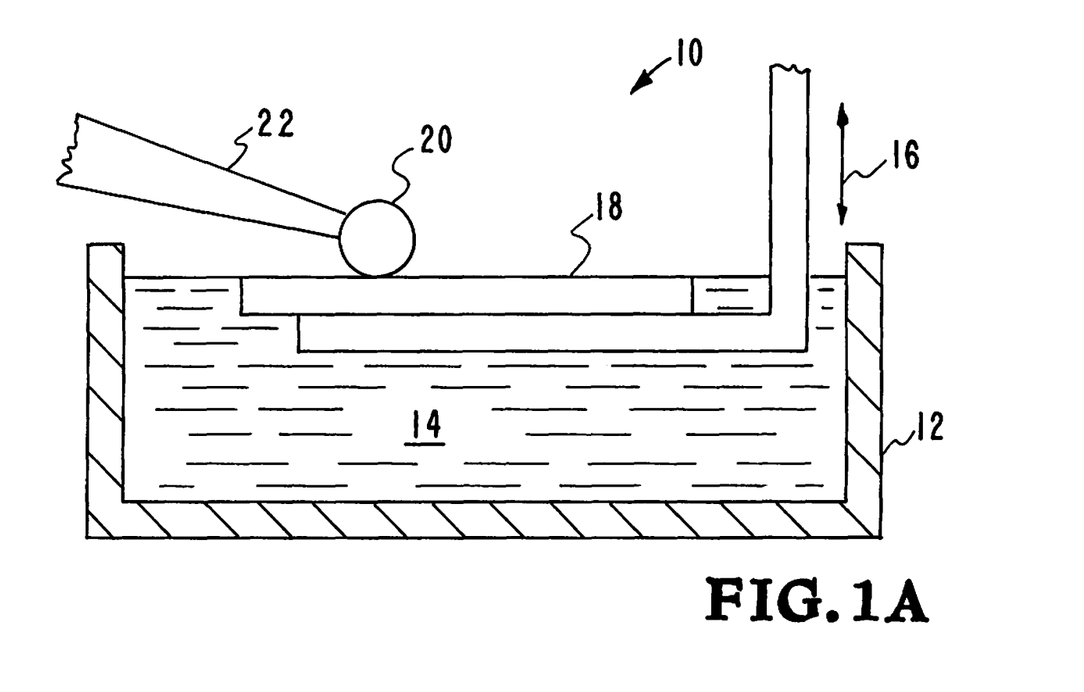
FIGS. 1A through 1H illustrate one embodiment of the inventor's emulsion stereolithography and 3D printing of multimaterials and nanoscale material gradients apparatus, system and methods.

FIG. 1A illustrates the inventor's emulsion stereolithography and 3D printing of multimaterials and nanoscale material gradients system 10 in its basic form. The system 10 has a reservoir 12 that is filled with a carrier fluid 14. An elevator system 18 is adapted to move and position substrate 18. The elevator system 18 is shown adapted to position substrate 18 within the fluid 14 filled reservoir 12. A first small droplet 20 is delivered onto the substrate 18 using the droplet dispenser 22. The droplet dispenser 22 can be a pipette, a droplet maker, or other form of droplet dispensing. The first droplet 20 is a droplet of hydrogel. The functional constituent for building the product is included in the droplet along with the hydrogel. The first droplet contains less than ten 4 of hydrogel and functional constituent.

Figure 1B:
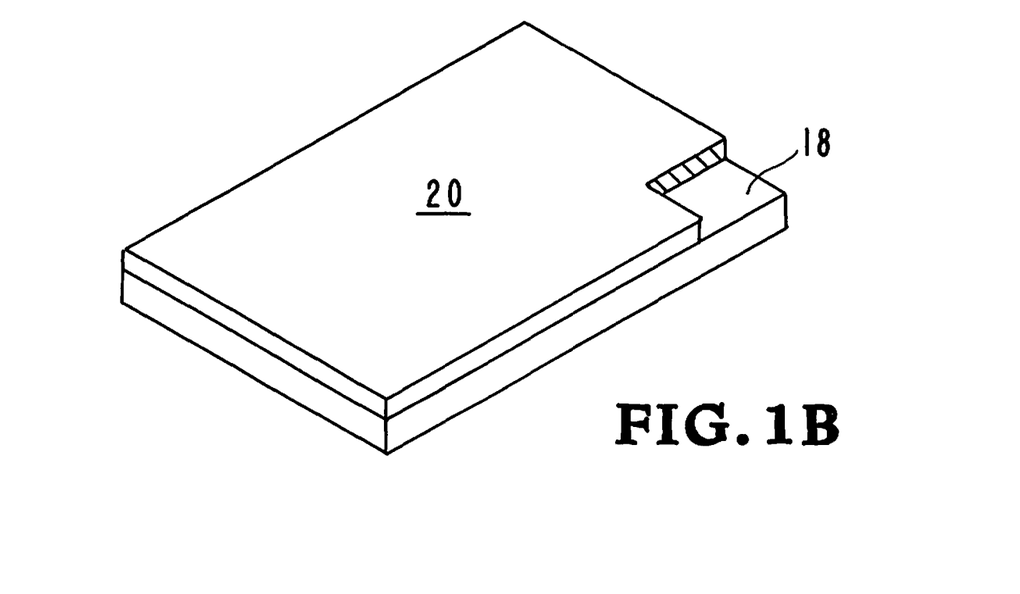

FIG. 1B is a top view of the substrate 18 of FIG. 1A showing the droplet 20 that has been deposited on substrate 18 has spread to encompasses the entire surface of the substrate 18. As illustrated in FIG. 1B, the first droplet 20 has spread to a thickness that is between 5-10 μm thick. The thickness of the disk droplet 20 depends upon the volume and viscosity of the hydrogel material 20.

Figure 1C:
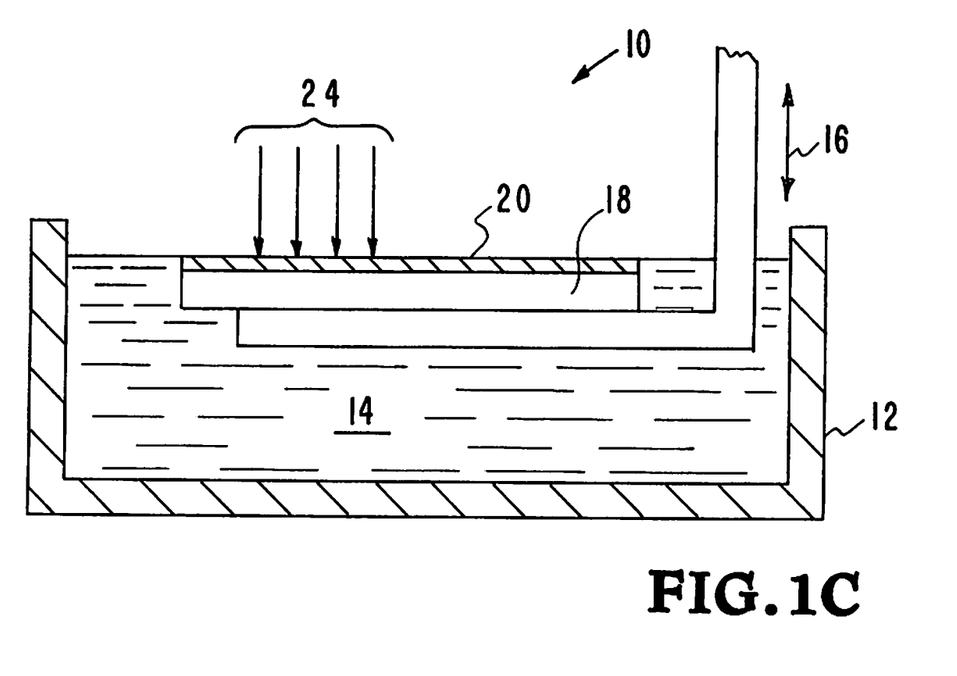

In FIG. 1C the elevator system 16 is illustrated having positioned the substrate 18 and the droplet 20 so that the droplet is surrounded by the carrier fluid 14. The hydrogel droplet 20 is only partially submerged in the polymer bath and the surface of the droplet is not covered by the carrier fluid 14. UV light 24 is focused onto the surface of the hydrogel droplet 20. The UV light 24 contains an image of the first layer of the product to be constructed. UV light 24 has been modulated from a DLP chip with the first CAD layer of the product to be constructed which is impinged onto the surface of the droplet 20 containing hydrogel and functional constituent to produce the first layer of the product.

Figure 1D:
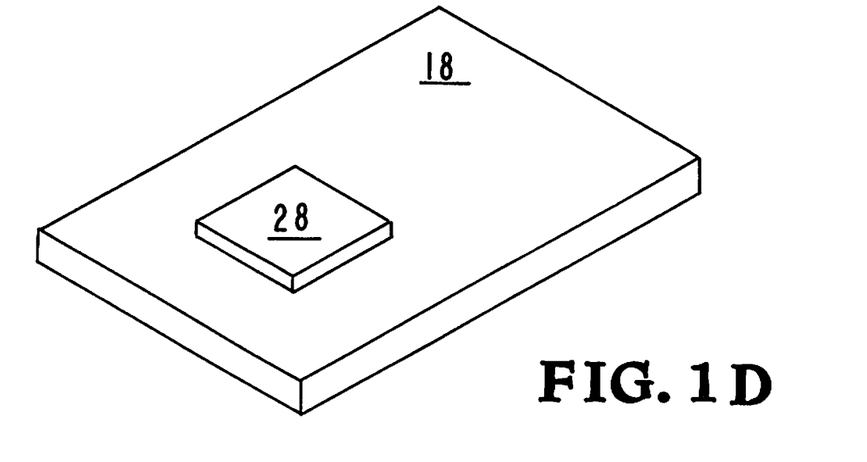

FIG. 1D is a top view of the substrate 18 of FIG. 1C showing the first layer 28 of the product to be constructed. As illustrated in FIG. 1D, the first layer 28 of the product to be constructed has taken the shape of the image of the first layer that was impinged onto the droplet 20 surface.

Figure 1E:
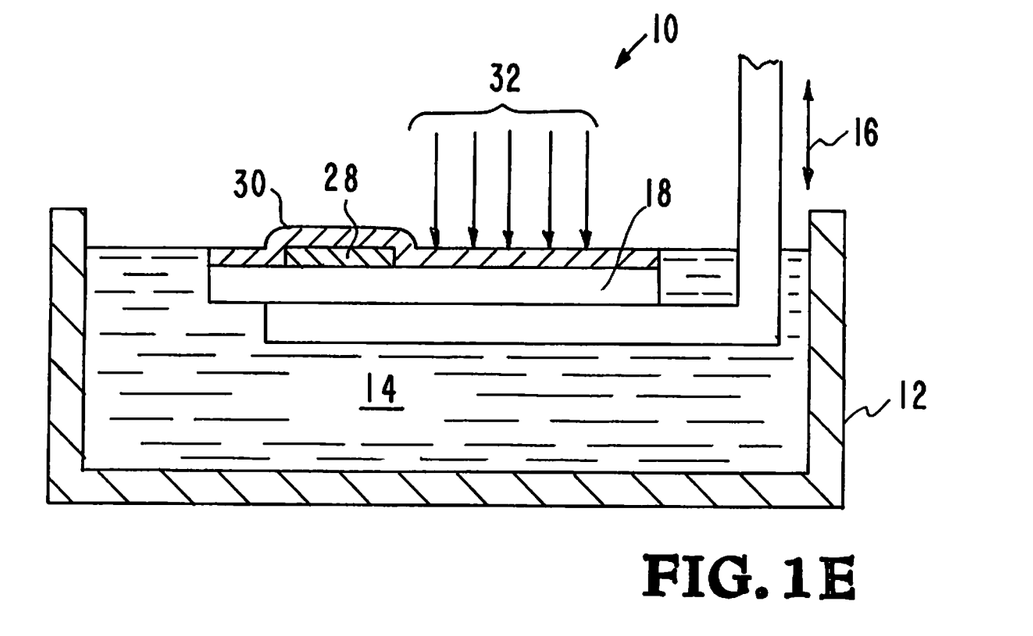

FIG. 1E illustrates the creation of a second layer onto the substrate 18. After the first layer 28 has solidified, a second droplet 30 is delivered onto the substrate 18 and first layer 28 using the droplet dispenser 22. The second droplet 30 is also a droplet of hydrogel and functional constituent. The second droplet 30 contains less than ten μL of hydrogel. A portion of the droplet 30 is positioned over the first layer 28 and a portion of the droplet 30 is adjacent the first layer 28. UV light 32 is focused onto the surface of the hydrogel droplet 30. The UV light 32 contains an image of the second layer of the product to be constructed. UV light 32 has been modulated from a DLP chip with the second CAD layer of the product to be constructed which is impinged onto the hydrogel droplet 30 surface and the second layer of the product to be constructed is solidified under a prescribed exposure dosage.

Figure 1F:
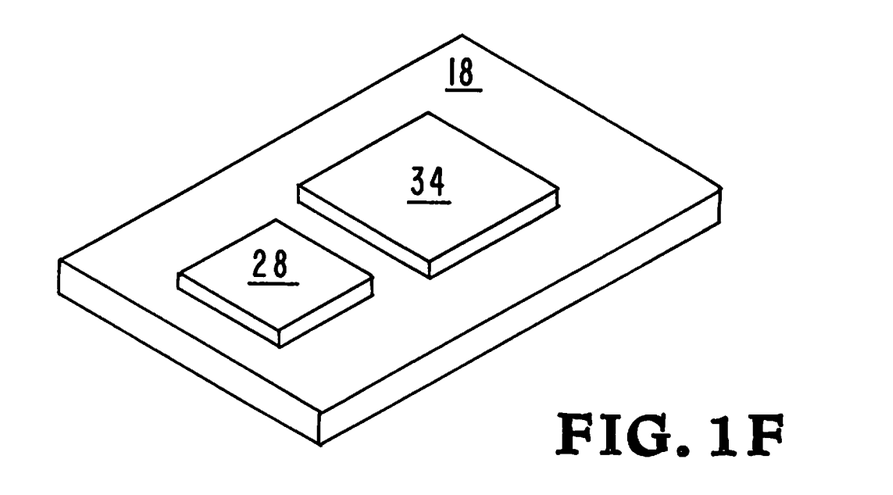

FIG. 1F is a top, view of the substrate 18 of FIG. 1E showing first layer 28 that has been deposited on substrate 18 and the second layer 34 that has been deposited on substrate 18. The second droplet 30 spread to a thickness that is between 5-10 μm thick. The thickness of the second droplet 30 depends upon the volume and viscosity of the hydrogel material 30. The focusing of UV light 32 on the second droplet of hydrogel material 30 produced the second layer 34.

Figure 1G:
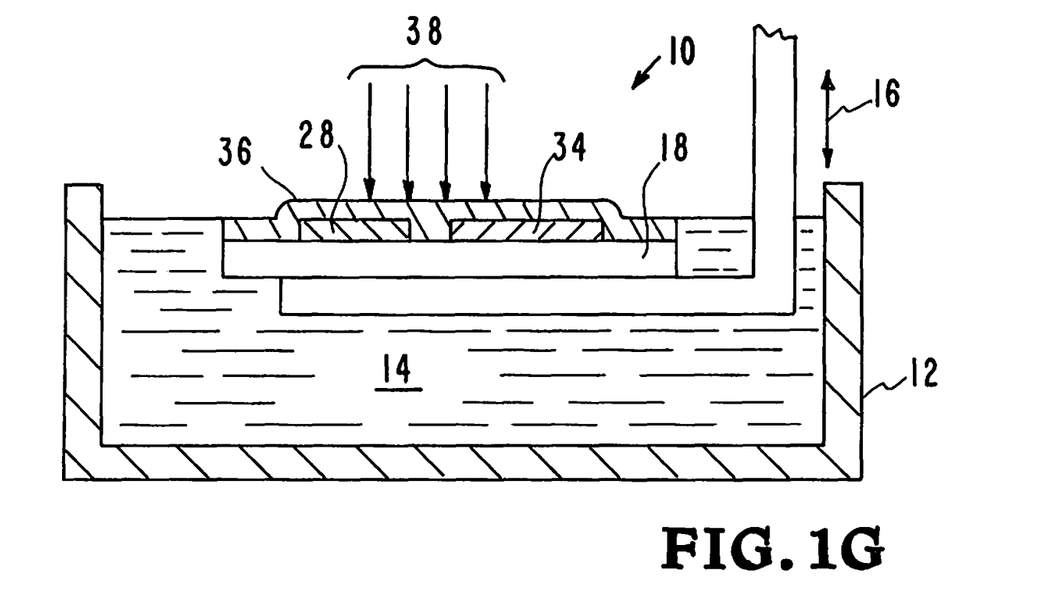

FIG. 1G illustrates the next step of the inventor's emulsion stereolithography and 3D printing of multimaterials and nanoscale material gradients system 10. FIG. 1G illustrates creating the third layer on the substrate 18. After the second layer 34 has solidified, a third small droplet 36 is delivered onto the substrate 18, the first layer 28, and the second layer 34 using the droplet dispenser 22. The third droplet 36 is also a droplet of hydrogel and functional constituent. The third droplet 36 contains less than ten μL of hydrogel. UV light 38 is focused onto the surface of the hydrogel droplet 36. The UV light 38 contains an image of the third layer of the product to be constructed. UV light 38 has been modulated from a DLP chip with the second CAD layer of the product to be constructed which is impinged onto the hydrogel droplet 36 surface and the third layer of the product to be constructed is solidified under a prescribed exposure dosage.

Figure 1H:
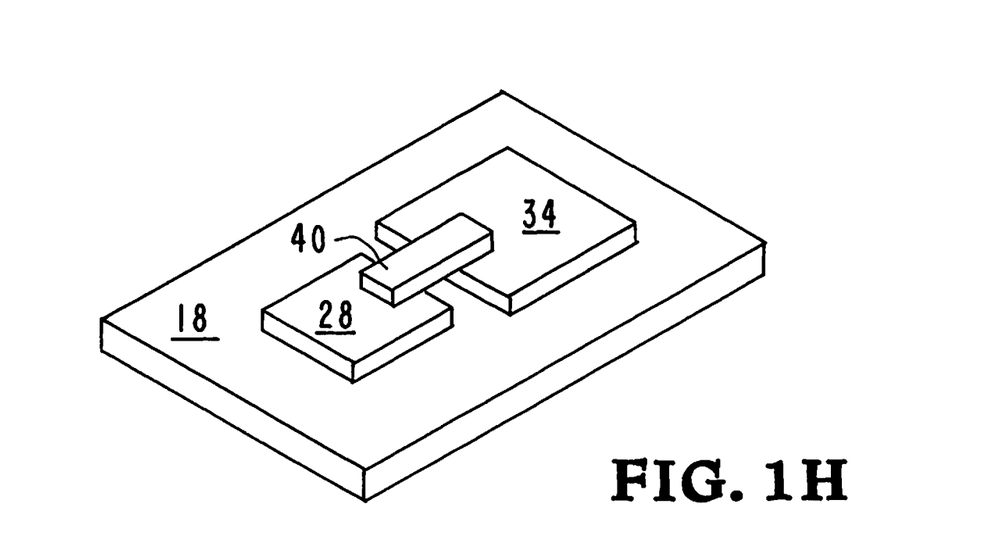

FIG. 1H is a top view of the substrate 18 showing that the third layer 40 has been deposited on substrate 18. FIG. 1H shows the third layer 40 of the product to be constructed has taken the shape of the image of the third layer that was impinged onto the hydrogel droplet 36 surface. The third layer 40 is adjacent the first layer 28 and the second layer 34.

Figure 2:
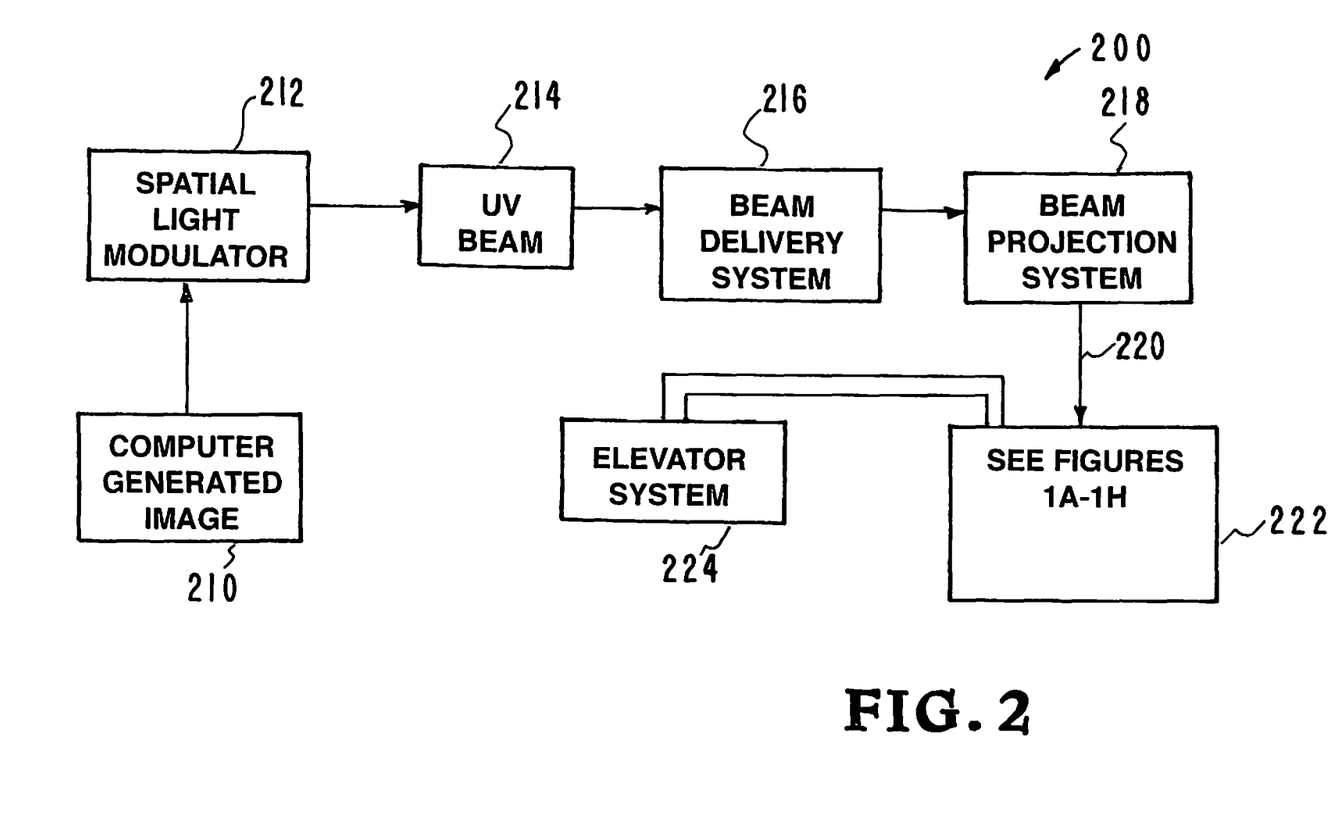
FIG. 2 illustrates the projection of images for emulsion stereolithography and 3D printing.

Referring to FIG. 2, an illustrative diagram shows the system wherein UV light containing an image of the individual layers of the product to be constructed is focused onto the hydrogel droplets. A series of steps are illustrated in the depiction of image of the individual layers being focused onto the hydrogel droplets.

In the first step 210, a computer generated image is produced. A 3D solid model of the product to be complete is designed by any suitable method, e.g., by bit mapping or by computer aided design (CAD) software at a PC/controller. The model is electronically sliced into series of 2-dimensional data files, i.e., 2D layers, each defining a planar cross section through the 3D preform of the complex product to be constructed, and which may be individually stored.

In the next step, step 212, a digital image of the first layer is projected by a spatial light modulator. A Lcos chip can be used for the projection. The next step, step 214, is the projection of a UV beam containing the digital image of the layers.

In the next step, step 216, a beam delivery system is used to produce a beam containing the digital images of the layers. The next step, step 218, uses a beam projection system to project the digital images of the layers onto the hydrogel droplets.

In the next step, step 222, the system of additive manufacturing illustrated in FIGS. 1A through 1H are used to build the product. After one layer is cured the composition and focusing optics undergo relative movement and the layer-by-layer process continues until all 3D layers of the product are completed.

Figure 3A:
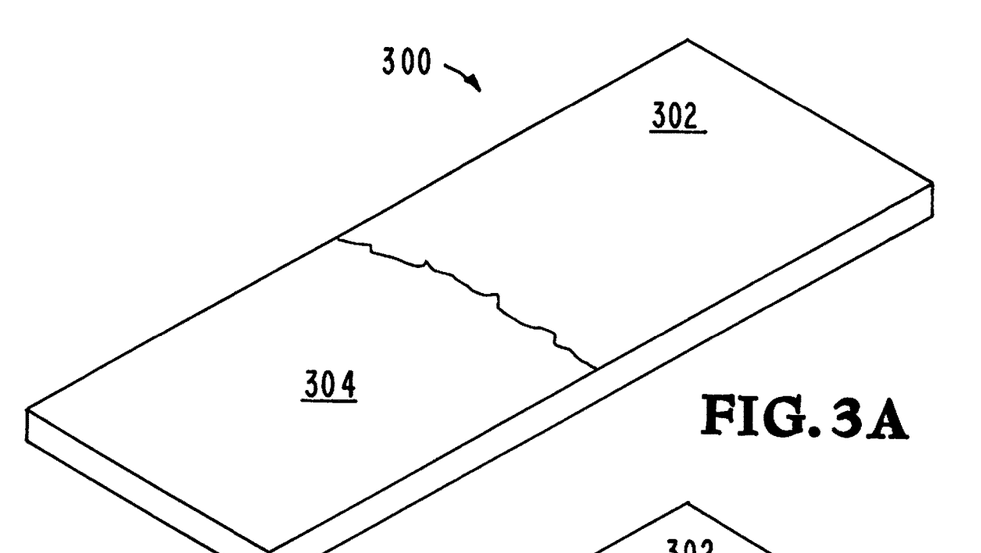
FIGS. 3A and 3B illustrate another embodiment of the inventor's emulsion stereolithography and 3D printing of multimaterials and nanoscale material gradients apparatus, system and methods.
Figure 3B:
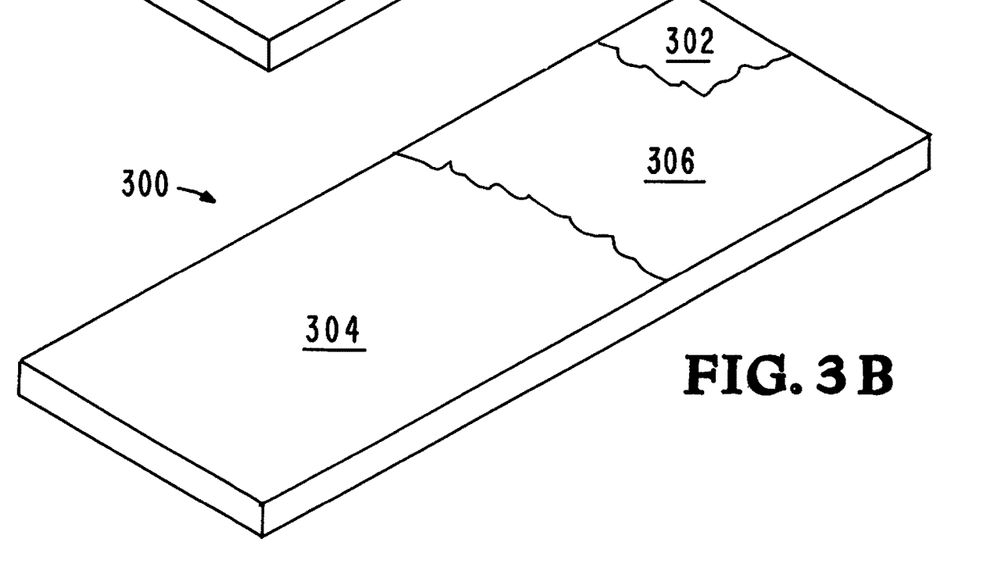

Referring to FIGS. 3A and 3B, another embodiment of the disclosed stereolithography and 3D printing of multimaterials and nanoscale material gradients system is illustrated. This embodiment is designated generally by the reference numeral 300. The embodiment 300 is substantially the same as the system 10 illustrated in FIGS. 1A through 1H except that the substrate 302 is substantially larger than the substrate 18 shown in FIGS. 1A through 1H. The large substrate allows more than one hydrogel droplet to be placed side by side on the substrate 302.

FIG. 3A is a top view of the substrate 302 showing a droplet 304 that has been deposited on substrate 302 has spread to encompasses the a portion of the surface of the substrate 302. As illustrated in FIG. 3A, the droplet 304 has spread to a thickness that is between 5-10 μm thick. The thickness of the droplet 304 depends upon the volume and viscosity of the hydrogel material. The extent that the droplet 304 spreads on the portion of the substrate 302 also depends upon the volume and viscosity of the hydrogel material.

FIG. 3B is a top view of the substrate 302 showing the droplet 304 and a second droplet 306 that has been deposited on substrate 302. The second droplet 306 has spread to encompass the remaining portion of the surface of the substrate 302. As illustrated in FIG. 3B, the droplet 306 has spread to a thickness that is between 5-10 μm thick. The thickness of the droplet 306 depends upon the volume and viscosity of the hydrogel material. The extent that the droplet 306 spreads on the portion of the substrate 302 also depends upon the volume and viscosity of the hydrogel material.

Example 1—Building Artificial Organs

Figure 4:
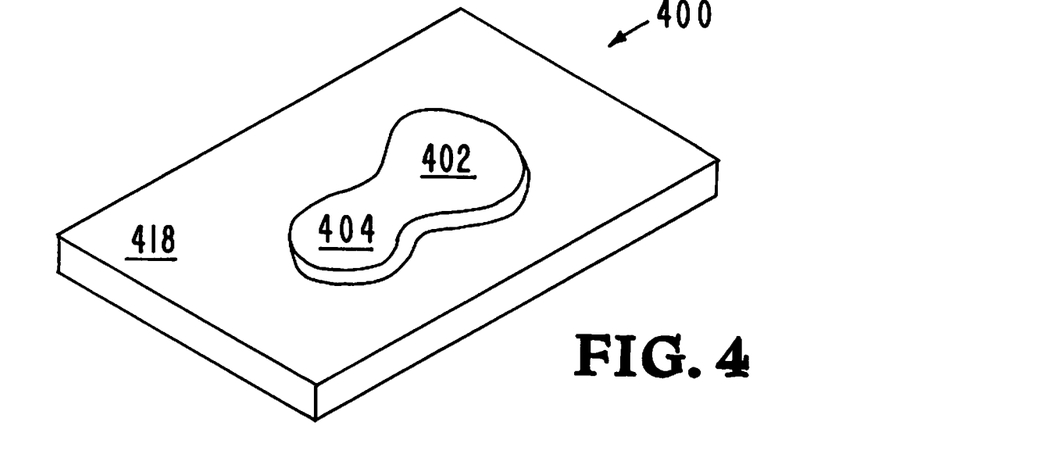
FIG. 4 illustrates an example of an enzyme array produced by the inventor's emulsion stereolithography and 3D printing of multimaterials and nanoscale material gradients apparatus, system and methods.

Referring to FIG. 4, an example 400 of the inventor's apparatus, systems, and methods enabling the fabrication of materials with embedded biomolecules for building of artificial organs is illustrated. FIG. 4 is a top view of a substrate 418 showing cells 402 and 404 that have been built on the substrate 418 with the cells containing enzymes. The cells 402 and 404 containing enzymes can be used for building artificial organs.

Using the inventor's apparatus, systems, and methods the cells 402 and 404 containing enzymes are constructed by pipetting individual micro- or nano-litter droplets with enzymes onto the substrate 418 followed by UV polymerization of the hydrogel. After step-by-step droplet delivery and the subsequent layer-by-layer UV polymerization via a digital mask the fabricated cells are completed.

Example 1—Building Active 3D Electronics 3D printing of active 3D electronics to date has been limited to specific plastics, passive conductors. The inventors' apparatus, systems, and methods will enable 3D printing of a diverse array of active 3D electronics such as electronic circuits, quantum dots, light emitting devices, 3D holographic displays and conducting polymers.

Figure 5:
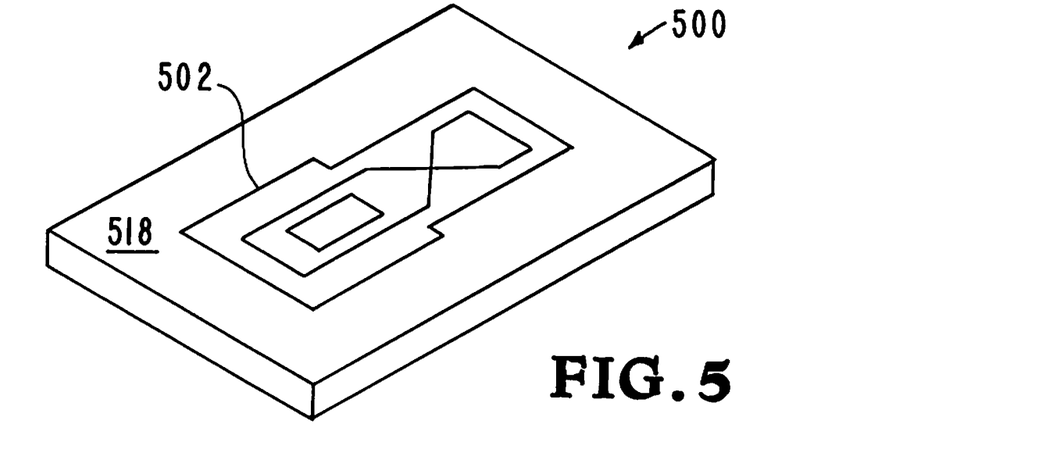
FIG. 5 illustrates an example of an electronic circuit produced by the inventor's emulsion stereolithography and 3D printing of multimaterials and nanoscale material gradients apparatus, system and methods.

Referring to FIG. 5, an example 500 of the inventor's apparatus, systems, and methods enabling the fabrication of electronic circuits is illustrated. FIG. 5 is a top view of a substrate 518 showing circuits 502 that have been built on the substrate 518 with the cells containing circuit material such as nanotubes.

Using the inventor's apparatus, systems, and methods the circuits 502 are constructed by pipetting individual micro- or nano-litter droplets onto the substrate 518 followed by UV polymerization of the hydrogel. After step-by-step droplet pipetting and the subsequent layer-by-layer UV polymerization via a digital mask the fabricated circuits 502 are completed.

Example 1—Building Multi-Color Sensor Arrays

Figure 6:
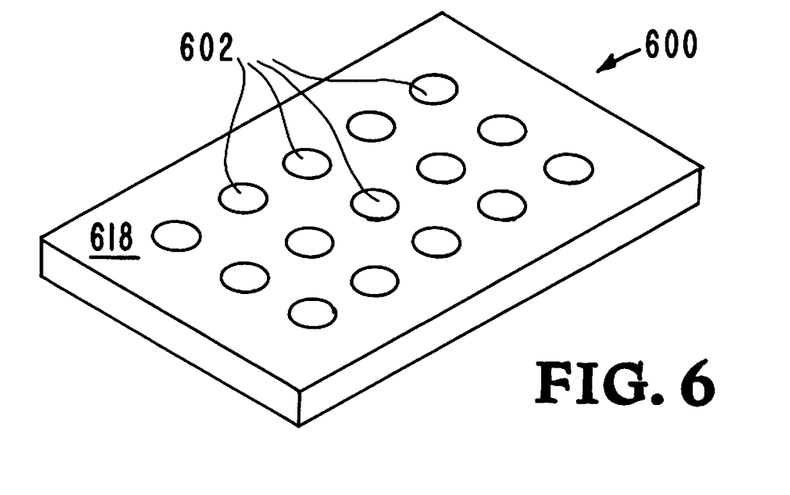
FIG. 6 illustrates an example of a multi-color sensor array produced by the inventor's emulsion stereolithography and 3D printing of multimaterials and nanoscale material gradients apparatus, system and methods.

Referring to FIG. 6, an example 600 the inventor's apparatus, systems, and methods enabling the fabrication of multi-color sensor arrays is illustrated. FIG. 6 is a top view of a substrate 618 showing multi-color sensor arrays 602 that have been built on the substrate 618 with the multi-color sensor arrays containing material that produce color display.

Using the inventor's apparatus, systems, and methods the multi-color sensor arrays are constructed by pipetting individual micro- or nano-litter droplets onto the substrate 618 followed by UV polymerization of the hydrogel. After step-by-step droplet pipetting and the subsequent layer-by-layer UV polymerization via a digital mask the fabricated multi-color sensor arrays 602 are completed.

Example 1—Building Nanotube Sensor Arrays

Figure 7:
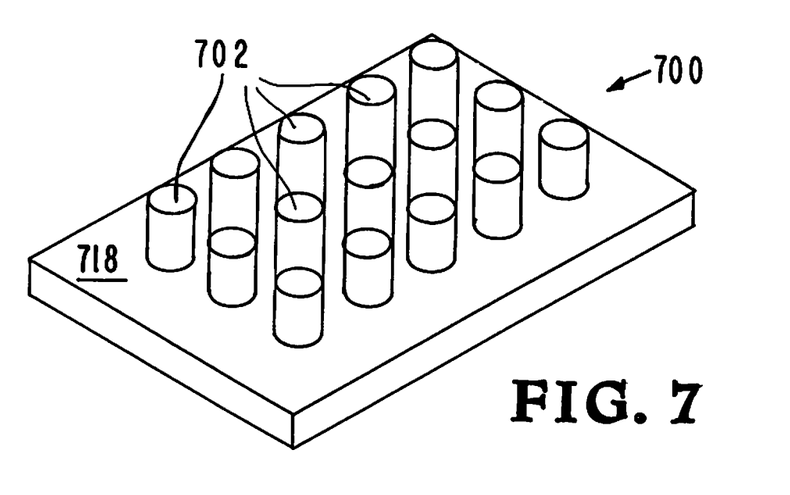
FIG. 7 illustrates an example of a nanotube sensor array produced by the inventor's emulsion stereolithography and 3D printing of multimaterials and nanoscale material gradients apparatus, system and methods.

Referring to FIG. 7, an example 700 the inventor's apparatus, systems, and methods enabling the fabrication of nanotube sensor arrays is illustrated. FIG. 7 is a top view of a substrate 718 showing nanotube sensor arrays 702 that have been built on the substrate 718 with the nanotube sensor arrays containing nanotube material that act as sensors.

Using the inventor's apparatus, systems, and methods the nanotube sensor arrays are constructed by pipetting individual micro- or nano-litter droplets onto the substrate 718 followed by UV polymerization of the hydrogel. After step-by-step droplet pipetting and the subsequent layer-by-layer UV polymerization via a digital mask the fabricated nanotube sensor arrays 702 are completed.

Example 1—Building 3D Tissue Growth Scaffolds

Figure 8A:
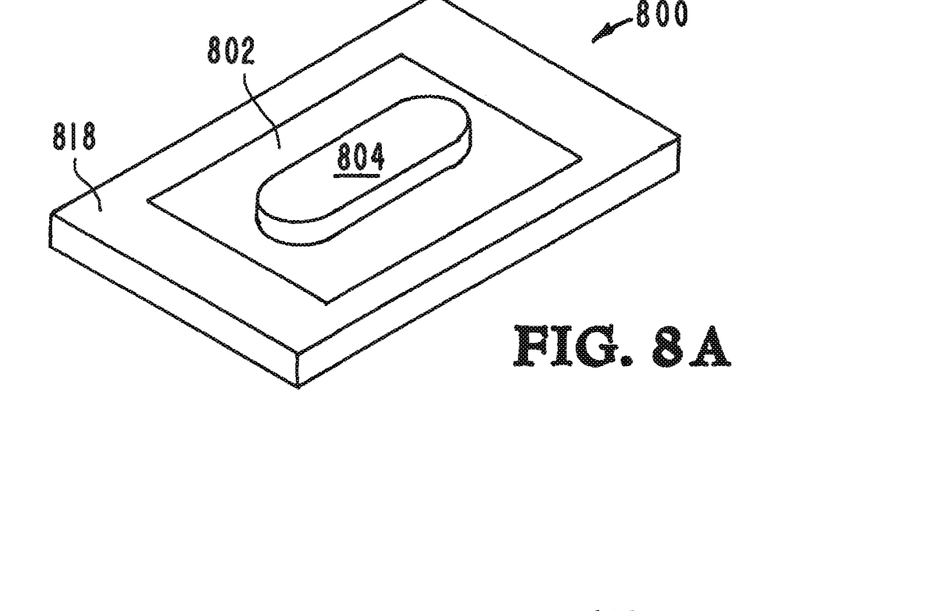
FIGS. 8A and 8B illustrate an example of a 3D tissue growth scaffold embedded with chemical gradients produced by the inventor's emulsion stereolithography and 3D printing of multimaterials and nanoscale material gradients apparatus, system and methods.
Figure 8B:
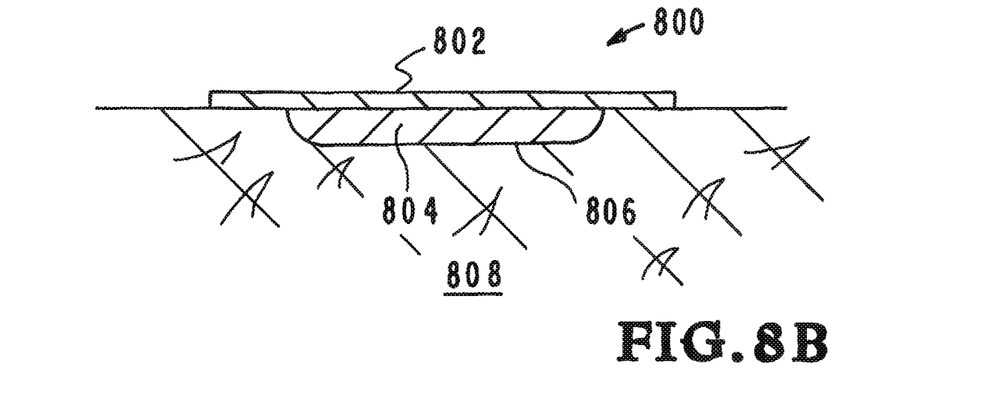

Referring to FIGS. 8A and 8B, an example 800 the inventor's apparatus, systems, and methods enabling the fabrication of tissue growth scaffolds is illustrated. FIG. 8A is a top view of a substrate 818 showing tissue growth scaffolds 802/804 that have been built on the substrate 818 with the tissue growth scaffolds tissue growth material 804.

Using the inventor's apparatus, systems, and methods the tissue growth scaffolds are constructed by pipetting individual micro- or nano-litter droplets onto the substrate 818 followed by UV polymerization of the hydrogel. After step-by-step droplet pipetting and the subsequent layer-by-layer UV polymerization via a digital mask the fabricated tissue growth scaffolds 802/804 are completed.

Although the description above contains many details and specifics, these should not be construed as limiting the scope of the application but as merely providing illustrations of some of the presently preferred embodiments of the apparatus, systems, and methods. Other implementations, enhancements and variations can be made based on what is described and illustrated in this patent document. The features of the embodiments described herein may be combined in all possible combinations of methods, apparatus, modules, systems, and computer program products. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination. Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described above should not be understood as requiring such separation in all embodiments.

Therefore, it will be appreciated that the scope of the present application fully encompasses other embodiments which may become obvious to those skilled in the art. In the claims, reference to an element in the singular is not intended to mean "one and only one" unless explicitly so stated, but rather "one or more." All structural and functional equivalents to the elements of the above-described preferred embodiment that are known to those of ordinary skill in the art are expressly incorporated herein by reference and are intended to be encompassed by the present claims. Moreover, it is not necessary for a device to address each and every problem sought to be solved by the present apparatus, systems, and methods, for it to be encompassed by the present claims. Furthermore, no element or component in the present disclosure is intended to be dedicated to the public regardless of whether the element or component is explicitly recited in the claims. No claim element herein is to be construed under the provisions of 35 U.S.C. 112, sixth paragraph, unless the element is expressly recited using the phrase "means for."

While the apparatus, systems, and methods may be susceptible to various modifications and alternative forms, specific embodiments have been shown by way of example in the drawings and have been described in detail herein. However, it should be understood that the application is not intended to be limited to the particular forms disclosed. Rather, the application is to cover all modifications, equivalents, and alternatives falling within the spirit and scope of the application as defined by the following appended claims.

The invention claimed is:

1. An additive manufacturing method of building a product, comprising the steps of:
   producing a computer generated three-dimensional (3D) image of the product;
   slicing the 3D image of the product into a series of data files defining planar cross sections of the product;
   using said data files to produce images of said series of individual slices of the product;
   providing a reservoir containing a carrier fluid;
   providing a substrate that has a substrate surface;
   providing an elevator system adapted to lower said substrate in said reservoir and in said carrier fluid;
   creating individual droplets of ultraviolet (UV) curable material and carbon nanotubes;
   delivering a single droplet of said UV curable material and carbon nanotubes onto said substrate surface using a droplet dispenser, wherein said substrate is in said reservoir containing said carrier fluid, and wherein said UV curable droplet and carbon nanotubes spread to encompass all of said substrate surface and form a disk on said substrate;
   using said elevator system to lower said substrate in said carrier fluid so that said disk is surrounded but not covered by said carrier fluid;
   projecting a first light beam onto said disk to solidify said disk, wherein said first light beam produces an image of a first slice of the product; and
   sequentially projecting additional light beams onto additional disks of UV curable material and carbon nanotubes in said reservoir to solidify said disks and to produce additional images of additional slices of the product.

2. An additive manufacturing method of building a product, comprising the steps of:
   producing a computer generated three-dimensional (3D) image of the product;
   slicing the 3D image of the product into a series of data files defining planar cross sections of individual slices, including a first slice, a second slice, and a third slice;
   using said data files for producing images of said series of individual slices including a first image of said first slice, a second image of said second slice, and a third image of said third slice;
   providing a reservoir containing a carrier fluid;
   providing a substrate that has a substrate surface;
   providing an elevator system adapted to lower said substrate in said carrier fluid in said reservoir;
   creating droplets of ultraviolet (UV) curable material and functional constituents including a first droplet, a second droplet, and a third droplet, wherein said droplets each contain less than ten µL of said UV curable material and functional constituents;
   using a droplet dispenser for delivering said first droplet onto said substrate surface, wherein said first droplet spreads to encompass all of said substrate surface and forms a first disk on said substrate surface;
   using said elevator system to lower said substrate in said carrier fluid so that said first disk is surrounded but not covered by said carrier fluid;
   projecting a first light beam onto said first disk in said reservoir, wherein said first light beam solidifies said first disk and produces first image of said first slice to build a first layer of the product;
   using said droplet dispenser for delivering said second droplet onto said first layer, or on-to said substrate surface in said reservoir, or delivering said second droplet onto both said first layer and said substrate surface in said reservoir, wherein said second droplet spreads to encompass all of said substrate surface or said first layer and forms a second disk;
   using said elevator system to lower said substrate in said carrier fluid so that said second disk is surrounded but not covered by said carrier fluid;
   projecting a second light beam onto said second disk in said reservoir, wherein said second light beam solidifies said second disk and produces said second image of said second slice of the product to build said second layer of the product;
   using said droplet dispenser for delivering said third droplet onto said second layer, or onto said substrate surface in said reservoir, or delivering said third droplet onto both said second layer and said substrate surface in said reservoir, wherein said third droplet spreads to encompass all of said substrate surface or said second layer and forms a third disk;
   using said elevator system to lower said substrate in said carrier fluid so that said third disk is surrounded but not covered by said carrier fluid; and
   projecting a third light beam onto said third disk in said reservoir, wherein said third light beam solidifies said third disk and produces said third image of said third slice to build a third layer of the product.

* * * * *